US012409070B2

(12) United States Patent
Ladas

(10) Patent No.: US 12,409,070 B2
(45) Date of Patent: Sep. 9, 2025

(54) APPARATUS AND METHOD FOR CORNEAL REFRACTIVE OPTIMIZATION USING POST-OPERATIVE MEASUREMENTS

(71) Applicant: Advanced Euclidean Solutions, LLC., Wilmington, DE (US)

(72) Inventor: John Gregory Ladas, Germantown, MD (US)

(73) Assignee: Advanced Euclidean Solutions, LLC., Wilmington, DE (US)

( * ) Notice: Subject to any disclaimer, the term of this patent is extended or adjusted under 35 U.S.C. 154(b) by 303 days.

(21) Appl. No.: 17/595,907

(22) PCT Filed: May 29, 2020

(86) PCT No.: PCT/US2020/035238
§ 371 (c)(1),
(2) Date: Nov. 29, 2021

(87) PCT Pub. No.: WO2020/243508
PCT Pub. Date: Dec. 3, 2020

(65) Prior Publication Data
US 2022/0313487 A1  Oct. 6, 2022

Related U.S. Application Data

(60) Provisional application No. 62/855,364, filed on May 31, 2019.

(51) Int. Cl.
*A61F 9/008*     (2006.01)
*G16H 20/40*     (2018.01)

(52) U.S. Cl.
CPC ........ *A61F 9/0084* (2013.01); *A61F 9/00827* (2013.01); *G16H 20/40* (2018.01);
(Continued)

(58) Field of Classification Search
CPC ................ A61F 9/0084; A61F 9/00827; A61F 2009/00872; A61F 2009/0088; A61F 2009/00882; G16H 20/40
See application file for complete search history.

(56) References Cited

U.S. PATENT DOCUMENTS

2003/0208190 A1*  11/2003  Roberts ............... A61F 9/00806
                                                      606/5
2005/0107775 A1    5/2005  Huang et al.
(Continued)

FOREIGN PATENT DOCUMENTS

CN    108888407 A    11/2018
CN    109300548 A    2/2019
(Continued)

OTHER PUBLICATIONS

Written Opinion and International Search Report issued by the International Search Authority in related International Patent Application PCT/US2020/035238, dated Aug. 27, 2020.

*Primary Examiner* — Lynsey C Eiseman
*Assistant Examiner* — Skylar Lindsey Christianson
(74) *Attorney, Agent, or Firm* — ArentFox Schiff LLP

(57) ABSTRACT

The disclosure provides methods and apparatuses for determining a laser parameter set for corneal refractive surgery. The apparatus may include an autorefractor configured to obtain at least two ocular measurement parameters for an eye and to obtain a post-operative refraction of the eye. The apparatus may include a user interface configured to obtain a target refraction for the eye. The apparatus may include a memory and a processor communicatively coupled to the user interface, the autorefractor, and the memory. The processor may be configured to determine the laser parameter set based on an algorithm using the at least two ocular measurement parameters. The processor may be configured (Continued)

to correlate the at least two ocular measurement parameters, the laser parameter set, and the post-operative refraction as a training set.

19 Claims, 8 Drawing Sheets

(52) U.S. Cl.
CPC ............. *A61F 2009/00872* (2013.01); *A61F 2009/0088* (2013.01); *A61F 2009/00882* (2013.01)

(56) References Cited

U.S. PATENT DOCUMENTS

| | | |
|---|---|---|
| 2010/0114077 A1 | 5/2010 | Dai |
| 2018/0161098 A1* | 6/2018 | Gupta .................... G06N 20/20 |
| 2019/0099262 A1* | 4/2019 | Ladas ................... A61F 2/1613 |
| 2019/0307554 A1* | 10/2019 | Schuele ............... A61F 2/1602 |
| 2020/0155351 A1* | 5/2020 | Lobanoff ............. A61B 3/1035 |

FOREIGN PATENT DOCUMENTS

| | | |
|---|---|---|
| WO | WO 03082162 A2 | 10/2003 |
| WO | WO2015054414 A1 | 4/2015 |

* cited by examiner

FIG. 3

APPARATUS AND METHOD FOR CORNEAL REFRACTIVE OPTIMIZATION USING POST-OPERATIVE MEASUREMENTS

CLAIM OF PRIORITY UNDER 35 U.S.C. § 119

This application is a National Stage entry of the International Application No. PCT/US2020/035238, filed May 29, 2020, which claims priority to U.S. Provisional Application No. 62/855,364 titled "APPARATUS AND METHOD FOR CORNEAL REFRACTIVE OPTIMIZATION USING POST-OPERATIVE MEASUREMENTS," filed May 31, 2019, which is assigned to the assignee hereof, and incorporated herein by reference in its entirety.

FIELD OF THE INVENTION

Aspects of the present invention relate to systems, apparatuses, and methods for selecting a laser parameter set for corneal refractive surgery.

BACKGROUND

Corneal refractive surgery may utilize a laser to ablate, remove, or shape a portion of the cornea to change a refraction of an eye. Example corneal refractive surgery techniques include laser-assisted in-situ keratomileusis (LASIK) and Small Incision Lenticule Extraction (SMILE). Multiple algorithms for determining laser parameters for corneal refractive surgery are currently available. For example, wavefront guided profile, a wavefront-optimized profile, or a topography-guided profile may be considered algorithms for determining laser parameters. Although the existing algorithms give similar results over a range of input parameters, they also diverge significantly at specified ranges of input parameters.

Individual algorithms have been demonstrated to work best with certain input parameters. The input parameters may include ocular measurement parameters such as axial length, corneal power, a white-to-white distance, gender or sex, anterior chamber depth, pre-operative refraction, and/or lens thickness. For example, a particular algorithm may work better with "shorter" eyes and another particular algorithm may work better in "longer" eyes. Further, "adjustments" to these algorithms may be used to obtain better results. An "adjustment" may include any additional factor applied to a laser parameter calculation algorithm.

The current state of the art includes selecting one algorithm to determine the laser parameters and possibly comparing the results to those obtained using another algorithm. A limited number of ophthalmologists understand the data and literature that support using one algorithm over another. While the use of a particular algorithm may be debatable, there are certain scenarios (e.g., a specific measured axial length or corneal power) in which one algorithm is generally accepted as better than others.

SUMMARY

Aspects of the present disclosure may include apparatuses and methods for determining laser parameter sets for corneal refractive surgery. A first method may include determining one or more targets for corneal refractive surgery. The method may include obtaining at least two ocular measurement parameters. The method may include determining a laser parameter set based on an algorithm using the at least two ocular measurement parameters and the one or more targets for corneal refractive surgery. The method may include determining an estimated error of the algorithm using a deep learning machine trained on verified post-operative results. The method may include adjusting the targets for corneal refractive surgery based on the estimated error. The method may include redetermining the laser parameter set for corneal refractive surgery.

A second method of laser parameter set selection may include obtaining at least two ocular measurement parameters for an eye by an autorefractor. The method may include determining one or more targets for corneal refractive surgery. The method may include determining a laser parameter set based on an algorithm using the at least two ocular measurement parameters. The method may include obtaining a post-operative refraction of the eye from the autorefractor. The method may include correlating the at least two ocular measurement parameters, the laser parameter set, and the post-operative refraction as a training set.

In another aspect, the disclosure provides a non-transitory computer-readable medium storing computer executable instructions. The instructions may be executed by a computer to obtain at least two ocular measurement parameters for an eye by an autorefractor or wavefront analyzer. The computer-readable medium may store instructions to determine one or more targets for corneal refractive surgery. The computer-readable medium may store instructions to determine a laser parameter set based on an algorithm using the at least two ocular measurement parameters. The computer-readable medium may store instructions to obtain a post-operative refraction of the eye from the autorefractor or the wavefront analyzer. The computer-readable medium may store instructions to correlate the at least two ocular measurement parameters, the laser parameter set, and the post-operative refraction as a training set.

In another aspect, the disclosure provides an apparatus for determining a laser parameter set for corneal refractive surgery. The apparatus may include an autorefractor configured to obtain at least two ocular measurement parameters for an eye and to obtain a post-operative refraction of the eye. The apparatus may include a user interface configured to obtain a target refraction for the eye. The apparatus may include a memory and a processor communicatively coupled to the user interface, the autorefractor, and the memory. The processor may be configured to determine the laser parameter set based on an algorithm using the at least two ocular measurement parameters. The processor may be configured to correlate the at least two ocular measurement parameters, the laser parameter set, and the post-operative refraction as a training set.

Additional advantages and novel features relating to aspects of the present invention will be set forth in part in the description that follows, and in part will become more apparent to those skilled in the art upon examination of the following or upon learning by practice thereof.

BRIEF DESCRIPTION OF THE FIGURES

In the drawings:

FIG. 3 illustrates an example input user interface for use in accordance with aspects of the present disclosure.

DETAILED DESCRIPTION

Aspects of the present disclosure may include systems, apparatuses, and methods for determining a laser parameter set for corneal refractive surgery, which may include laser-assisted in-situ keratomileusis (LASIK), Small Incision Lenticule Extraction (SMILE), or other procedures that ablate, remove, or shape a portion of the cornea. A laser parameter set may refer to any parameters used to configure a device for performing a corneal refractive surgery. For example, in a LASIK procedure using an excimer laser, the laser parameter set may be referred to as an ablation profile and may include one or more of: ablation diameter, ablation depth, ablation blend zone, corneal flap thickness, residual corneal bed, excimer fluence level, femtosecond laser flap size, or which femtosecond laser to use for flap. As another example, for a SMILE procedure, the laser parameter set may include one or more of: lenticule size/diameter, lenticule thickness, lenticule profile, corneal roof thickness, residual corneal bed, lenticule extraction tunnel size, femtosecond laser energy setting, or femtosecond laser spot size/spacing. In an aspect, post-treatments results may be utilized to train a machine-learning model (e.g., a neural network) to predict an error (e.g., a difference between a target and a post-treatment result) due to use of an existing algorithm for determining the laser parameter set. The parameters of the algorithm may be modified based on the predicted error to reduce the error. The post-treatment results may be used to further train the machine-learning and improve results.

Figure 1:
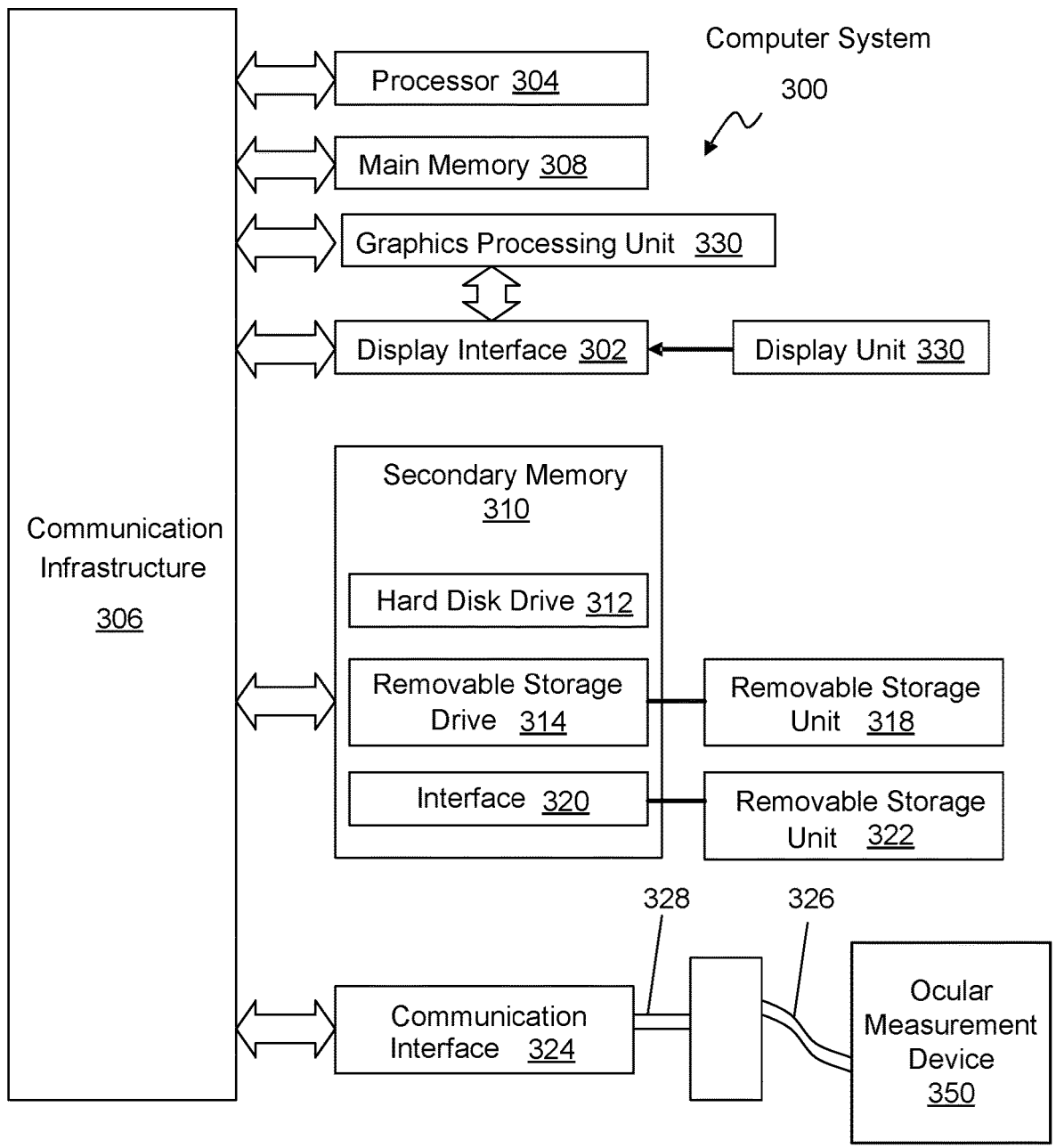
FIG. 1 illustrates various features of an example computer system for use in conjunction with aspects of the present disclosure.

Aspects of the present disclosure may be implemented using hardware, software, or a combination thereof and may be implemented in one or more computer systems or other processing systems. In an aspect of the present disclosure, features are directed toward one or more computer systems capable of carrying out the functionality described herein. An example of such a computer system 300 is shown in FIG. 1.

Computer system 300 includes one or more processors, such as processor 304. The processor 304 is connected to a communication infrastructure 306 (e.g., a communications bus, cross-over bar, or network). Various software aspects are described in terms of this example computer system. After reading this description, it will become apparent to a person skilled in the relevant art(s) how to implement aspects of the disclosure using other computer systems and/or architectures.

Computer system 300 can include a display interface 302 that forwards graphics, text, and other data from the communication infrastructure 306 (or from a frame buffer not shown) for display on a display unit 330. For example, the display interface 302 may forward a graphical rendering of a super surface from the processor 304 to the display unit 330. Computer system 300 also includes a main memory 308, preferably random access memory (RAM), and may also include a secondary memory 310. The secondary memory 310 may include, for example, a hard disk drive 312 and/or a removable storage drive 314, representing a floppy disk drive, a magnetic tape drive, an optical disk drive, a universal serial bus (USB) flash drive, etc. The removable storage drive 314 reads from and/or writes to a removable storage unit 318 in a well-known manner. Removable storage unit 318 represents a floppy disk, magnetic tape, optical disk, USB flash drive, etc., which is read by and written to removable storage drive 314. As will be appreciated, the removable storage unit 318 includes a computer usable storage medium having stored therein computer software and/or data.

Alternative aspects of the present disclosure may include secondary memory 310 and may include other similar devices for allowing computer programs or other instructions to be loaded into computer system 300. Such devices may include, for example, a removable storage unit 322 and an interface 320. Examples of such may include a program cartridge and cartridge interface (such as that found in video game devices), a removable memory chip (such as an erasable programmable read only memory (EPROM), or programmable read only memory (PROM)) and associated socket, and other removable storage units 322 and interfaces 320, which allow software and data to be transferred from the removable storage unit 322 to computer system 300.

Computer system 300 may also include a communications interface 324. Communications interface 324 allows software and data to be transferred between computer system 300 and external devices. Examples of communications interface 324 may include a modem, a network interface (such as an Ethernet card), a communications port, a Personal Computer Memory Card International Association (PCMCIA) slot and card, etc. Software and data transferred via communications interface 324 are in the form of signals 328, which may be electronic, electromagnetic, optical or other signals capable of being received by communications interface 324. These signals 328 are provided to communications interface 324 via a communications path (e.g., channel) 326. This path 326 carries signals 328 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 314 and a hard disk installed in hard disk drive 312. These computer program products provide software to the computer system 300. Aspects of the present disclosure are directed to such computer program products.

In an aspect, the computer system 300 may include an ocular measurement device 350. The ocular measurement device 350 may determine one or more ocular measurement parameters. An ocular measurement device may include any device for measuring an eye. For example, the ocular measurement device 350 may measure corneal power (keratometry), corneal topography, corneal tomography, corneal pachymetry, refraction, cyclopegia refraction, and wavefront refraction. Additionally, the ocular measurement device 350 may include an ocular measurement device such as a wavefront analyzer, which may perform corneal topography. The ocular measurement device 350 may further receive input of ocular measurement parameters (e.g., gender or sex). In some implementations, the ocular measurement device 350 may measure an axial length and a corneal power of an eye. In an aspect, the ocular measurement device 350 may further measure a white-to-white distance, anterior chamber depth, pre-operative refraction, and/or lens thickness. The axial length may be a distance from the surface of the cornea to the retina. The corneal power may be a dioptric power of the cornea. As another example, the ocular measurement device 350 may measure an anterior chamber depth of an eye. In an aspect, the ocular measurement device 350 may be an ultrasound device. In another aspect, the ocular measurement device 350 may be an optical biometer. Various optical biometers are available under the names LENSTAR® and IOL MASTER. In another aspect, the ocular measurement device 350 may include an intraoperative abberrometry device. The intraoperative abberrometry device may take measurements of refractive properties of the eye during surgery. For example, an intraoperative abberrometry device may provide information on sphere, cylinder, and axis of the eye. The ocular measurement device 350 may be communicatively coupled to the processor 304 via the communication infrastructure 306, the communications interface 324, and/or the communications path 326.

Computer programs (also referred to as computer control logic) are stored in main memory 308 and/or secondary memory 310. Computer programs may also be received via communications interface 324. Such computer programs, when executed, enable the computer system 300 to perform the features in accordance with aspects of the present disclosure, as discussed herein. In particular, the computer programs, when executed, enable the processor 304 to perform the features in accordance with aspects of the present disclosure. Accordingly, such computer programs represent controllers of the computer system 300.

In an aspect of the present disclosure where the disclosure is implemented using software, the software may be stored in a computer program product and loaded into computer system 300 using removable storage drive 314, hard disk drive 312, or communications interface 320. The control logic (software), when executed by the processor 304, causes the processor 304 to perform the functions described herein. In another aspect of the present disclosure, the system is implemented primarily in hardware using, for example, hardware components, such as application specific integrated circuits (ASICs). Implementation of the hardware state machine so as to perform the functions described herein will be apparent to persons skilled in the relevant art(s).

In yet another aspect of the present disclosure, the disclosure may be implemented using a combination of both hardware and software.

Figure 2:
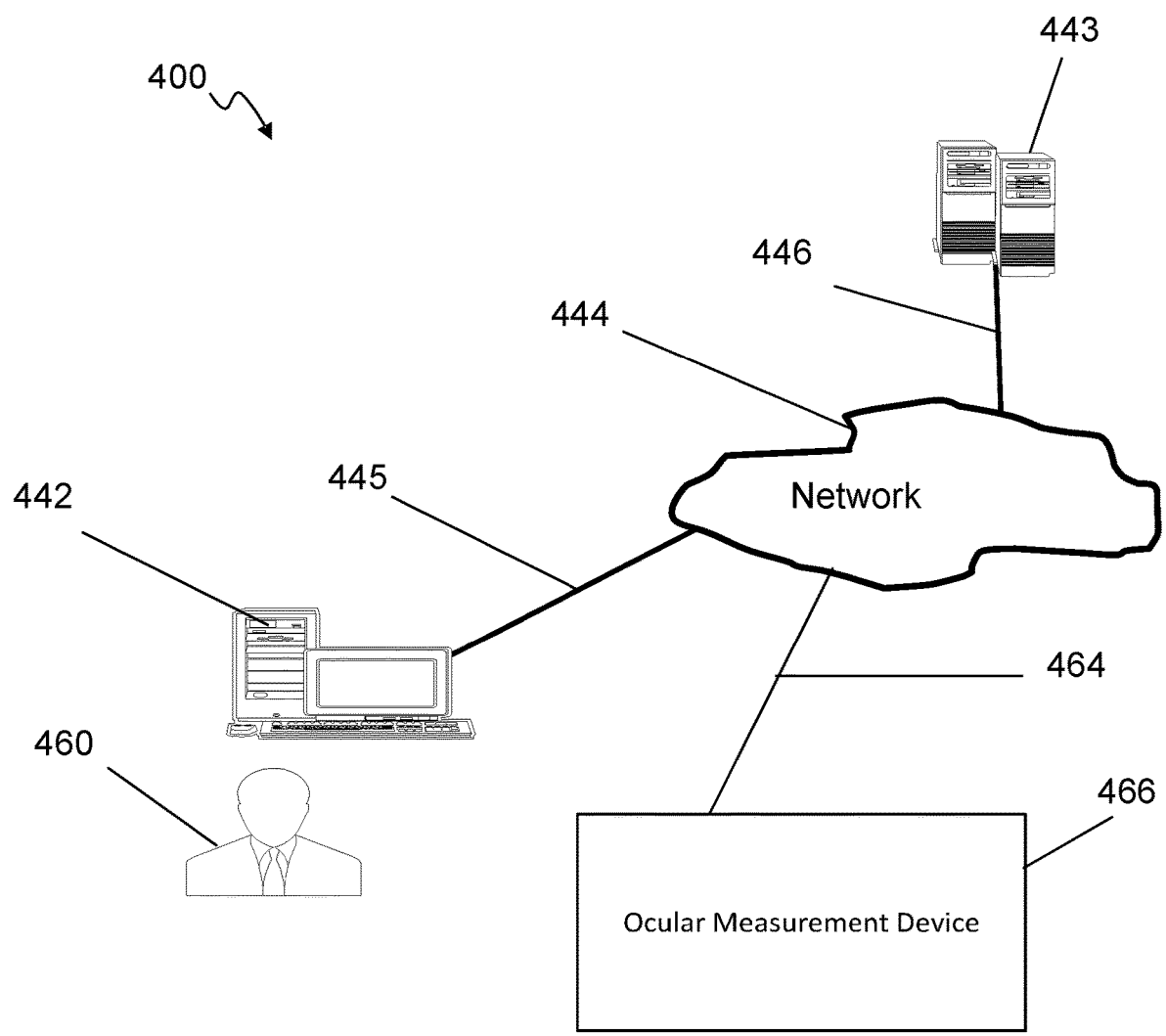
FIG. 2 illustrates an example system diagram of various hardware components and other features for use in accordance with aspects of the present disclosure.
Figure 3:
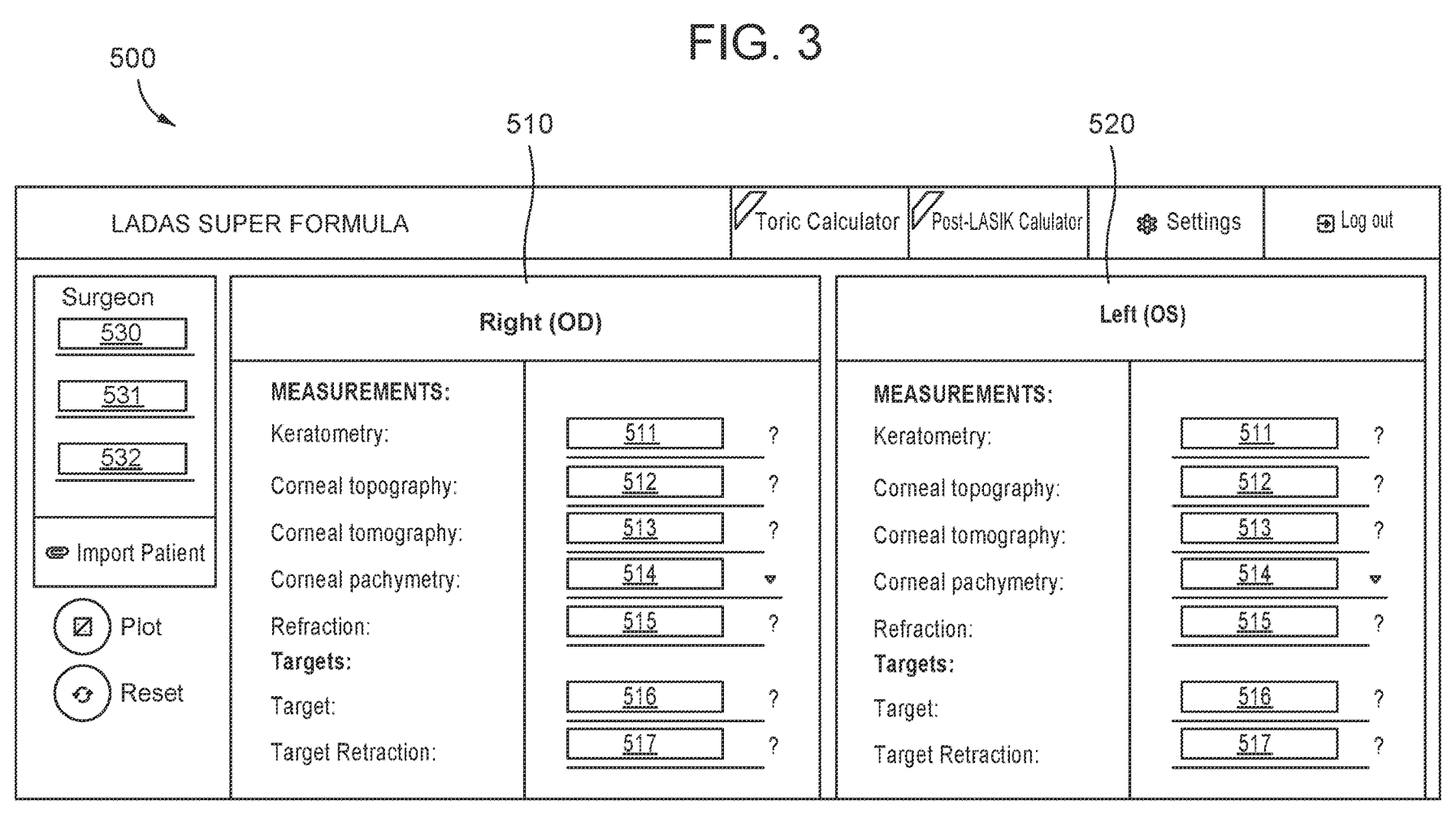

FIG. 2 shows a communication system 400 usable in accordance with aspects of the present disclosure. The communication system 400 includes one or more accessors 460 (also referred to interchangeably herein as one or more "users") and one or more terminals 442 and/or other input device or devices (e.g., an ocular measurement device 466). In an aspect, the ocular measurement device 466 may be similar to the ocular measurement device 350 (FIG. 3). The ocular measurement device 466 may further be configured to communicate with the network 444. In one aspect of the present disclosure, data for use is, for example, input and/or accessed after being received from an input device by accessors 460 via terminals 442, such as personal computers (PCs), minicomputers, mainframe computers, microcomputers, telephonic devices, or wireless devices, personal digital assistants ("PDAs") or a hand-held wireless devices (e.g., wireless telephones) coupled to a server 443, such as a PC, minicomputer, mainframe computer, microcomputer, or other device having a processor and a repository for data and/or connection to a repository for data, via, for example, a network 444, such as the Internet or an intranet, and/or a wireless network, and couplings 445, 446, 464. The couplings 445, 446, 464 include, for example, wired, wireless, or fiberoptic links. In another aspect of the present disclosure, the method and system of the present disclosure may include one or more features that operate in a stand-alone environment, such as on a single terminal.

In an aspect, the server 443 may be an example of the computer system 300 (FIG. 1). In an aspect, for example, the server 443 may be configured to perform the methods described herein. For example, the server 443 may obtain measurements such as an axial length and corneal power measurements from a terminal 442 and/or other input device. The server 443 may also determine one or more targets for corneal refractive surgery. For example, the measurements or the targets may be entered by an accessor 460, or provided by an ocular measurement device 350 (FIG. 1). The server 443 may determine a laser parameter set based on an algorithm using the at least two ocular measurement parameters and the one or more targets for corneal refractive surgery. Further, the server 443 may determine an estimated error of the algorithm using a deep learning machine trained on verified post-operative results. The server 443 may adjust the targets for corneal refractive surgery based on the estimated error and redetermine the laser parameter set for corneal refractive surgery.

FIG. 3 illustrates an example input user interface (UI) 500 for use in accordance with aspects of the present invention. The user interface 500 may be implemented by the server 443 and displayed on the terminal 442, for example. The user interface 500 may allow a user to enter pre-operative measurements of one or more eyes as well as target parameters. The user interface 500 allows simultaneous calculation and plotting of both eyes. Input-data may include the corneal power (keratometry), corneal topography, corneal tomography, corneal pachymetry, refraction, cyclopegia refraction, or wavefront refraction. Slight variations of the pre-operative measurements may be used by different surgeons or in different countries. The desired postop refraction are then selected and the optimized calculations are then performed. The target refraction may be a goal specified by the surgeon. For example, a target refraction of 0.0 may be used.

The user interface 500 may include an input field 510 for a right eye and an input field 520 for a left eye. Each input field 510,520 may include input fields for specific measurements or parameters. For example, the input field 510 may include corneal power (keratometry) field 511, corneal topography field 512, corneal tomography field 513, corneal pachymetry field 514, refraction field 515, which may include one or both of cyclopegia refraction or wavefront refraction. The input field 510 may also include targets for corneal refractive surgery including a target refraction field 517. The input fields 510, 520 may also include a help icon (e.g., "?") that provides a description of the measurement or parameter including allowed ranges. Some fields may use a drop-down menu to select a value.

Additionally, the user interface 500 may include a surgeon field 530, a patient field 531, and a patient ID field 532. The server 443 may generate records for the surgeon and patient based on the fields 530, 531, 532. The user interface 500 may also include an import option 540 that may allow a user to upload a file (e.g., a spreadsheet) including measurements and parameters for one or more patients. A dedicated toric calculator and a post-LASIK calculator may also be included.

Figure 4:
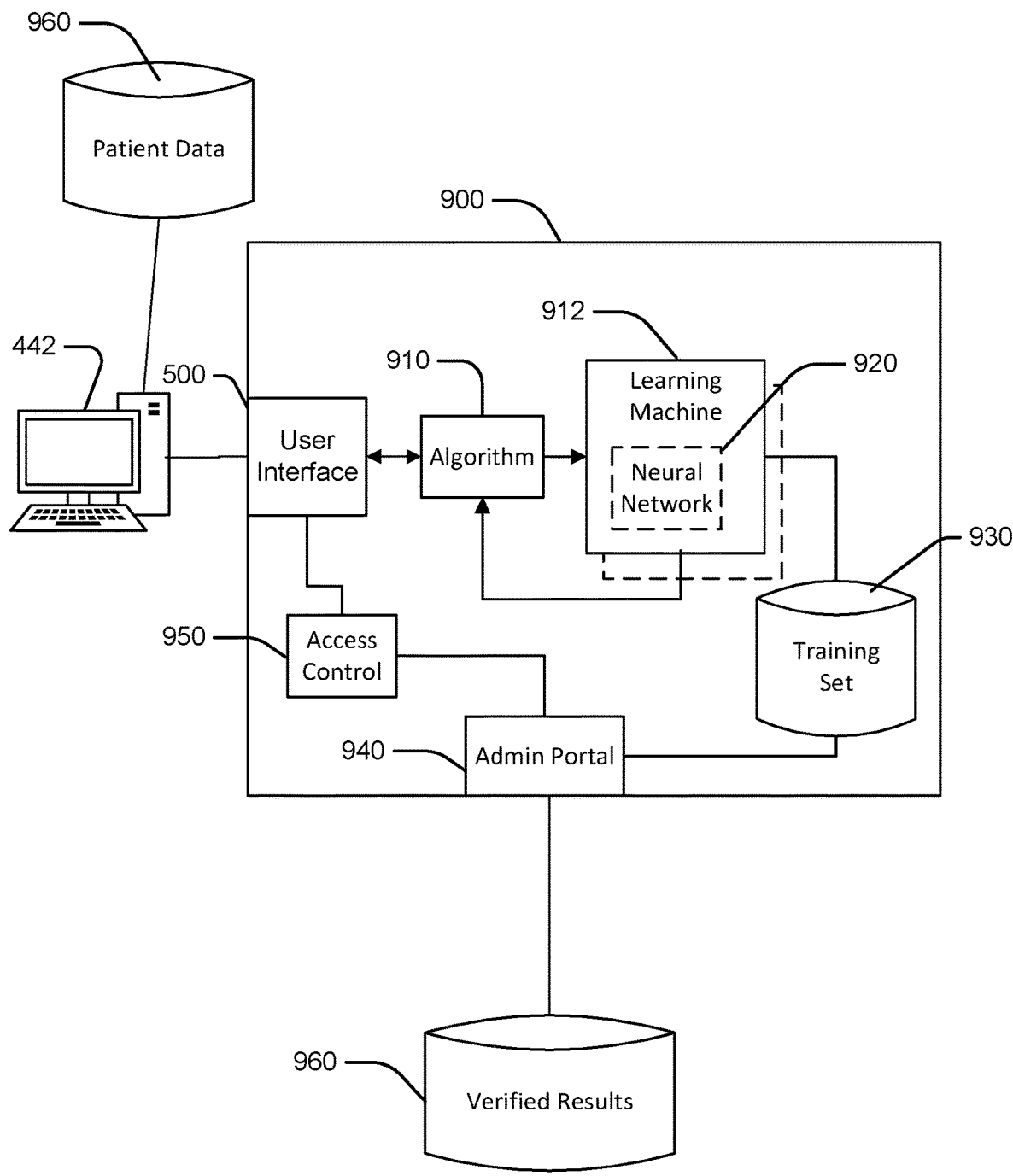
FIG. 4 is a diagram of an example computer system according to an aspect of the present disclosure.

Turning now to FIG. 4, an example system 900 may recommend a laser parameter set for corneal refractive surgery based on an algorithm and a trained deep learning machine 912. The system 900 may be implemented on a server 443, for example. The system 900 may communicate with one or more terminals 442 via the user interfaces 500 discussed above. The system 900 may include an algorithm component 910 for determining a laser parameter set based on an algorithm using at least two ocular measurement parameters, a deep learning machine 912 such as neural network 920 for determining an estimated error of the algorithm, and the user interface 500 for obtaining at least two ocular measurement parameters and a target for corneal refractive surgery. The algorithm component 910 may further adjust the target for corneal refractive surgery based on the estimated error and redetermine the laser parameter set based on the algorithm and the adjusted target for corneal refractive surgery. The system 900 may further include one or more training sets 930. The training sets 930 may include sets of post-operative data including two or more of the pre-operative measurements and parameters (e.g., corneal power (keratometry) field 511, corneal topography field 512, corneal tomography field 513, corneal pachymetry field 514, refraction field 515, which may include one or both of cyclopegia refraction or wavefront refraction). The training sets 930 may include the selected laser parameter set, and one or more target parameters (e.g., post-operative refraction). The training sets 930 may be used to train one or more of the deep learning machine 912 for estimating an error of a laser parameter set determined by the algorithm component 910, as explained in further detail below.

The system 900 may include an administrative portal 940 for controlling access to the system 900. For example, the administrative portal 940 may permit an administrative user to generate training sets 930 from verified results 960. The verified results 960 may be uploaded in the form of a database or spreadsheet. The administrative user may select combinations of measurements and parameters to use for the training sets 930. The administrative user may combine the uploaded verified results with any existing training sets 930. The system 900 may generate a new neural network 920 based on a new or updated training set 930. The system 900 may provide the administrative user with statistics regarding the neural network. For example, a neural network may be associated with input boundaries and correlation values. The administrative user may also configure access controls 950 to manage user accounts for different end users. The user accounts may be associated with saved patient data. Additionally, the user accounts may be associated with a customized neural network 920. For example, a customized neural network 920 may trained with verified results 960 exclusively from a particular surgeon, practice group, or laser manufacturer. A customized neural network 920 may help control for unknown or immeasurable factors affecting the particular surgeon, practice group, or laser manufacturer.

The algorithm component 910 may implement a laser parameter set determination algorithm. A laser parameter set determination algorithm may include any deterministic technique for generating a laser parameter set based on two or more ocular measurements. For example, the algorithm component 910 may include software executed by a processor to determine a laser parameter set according to an algorithm using input values from the user interface 500. For example, the algorithm component 910 may implement one or more of: a wavefront guided profile, a wavefront-optimized profile, or a topography-guided profile. The algorithm component 910 may provide the determined laser parameter set to the neural network 920 along with all of the input measurements and parameters. In an aspect, the algorithm component 910 may be implemented as a machine learned algorithm.

The learning machine 912 may use deep learning techniques to predict error of the algorithm component 910 based on the training set 930 including post-operative results. The learning machine 912 may be implemented by, for example, a neural network 920, which may utilize a Python based tensor flow. The neural network 920 may have a number of hidden layers, each including a number of neurons. The parameters of the neural network 920 may be selected based on results for a particular prediction. In an aspect, the learning machine 912 may include a computer processor (e.g., processor 304 that is programmed to execute instructions for developing the neural network 920 based on a network structure (e.g., number and type of layers). Once the learning machine 912 has trained the neural network 920 (or other learning machine), the processor configured with the trained learning machine 912 may determine the predicted error of the algorithm component 910 based the ocular measurement parameters. The neural network 920 may receive multiple numeric inputs to predict a single numeric output. In an implementation, the neural network may receive three numeric inputs (corneal power (keratometry), corneal topography, corneal tomography, corneal pachymetry, refraction, cyclopegia refraction, and wavefront refraction) and output an error value. The neural network 920 may be trained by one or more of the training set 930. The training sets 930 may be considered labelled data because the training sets 930 may include the post-operative refraction, which may be used to determine the accuracy or error of the algorithm. Accordingly, when the neural network 920 receives the set of numeric inputs, the neural network 920 may predict an estimated error of the algorithm component 910. The learning machine 912 may be implemented using different types of learning machines. For example, the learning machine 912 may use any combination of supervised and unsupervised learning techniques. The learning machine 912 may be structured as, for example, an artificial neural network, convolutional neural network, Bayesian network, or other deep learning model.

The algorithm component 910 may then adjust the algorithm inputs according to the predicted error. In particular, the algorithm component 910 may adjust a target (e.g., target post-op refraction) based on the predicted error. For example, the new target refraction may be set to the difference between the user input target refraction and the neural net predicted error. As an example, for an eye with a set of ocular measurement parameters and a target refraction, the neural network 920 may predict an error of 0.25. That is, when the algorithm component 910 calculates a laser parameter set for an eye with the set of ocular measurement parameters and target refraction of −0.5, then the eye will get re-calculated using the current algorithm component 910 but using the new target refraction value of −0.5−0.25=−0.75 instead of the user input target refraction. In other words, the algorithm component 910 may adjust one component of the algorithm's input (e.g., target refraction) by subtracting the neural network predicted error from the input value.

In an aspect, the learning machine 912 may identify one or more elements of a laser parameter set associated with an error. For example, the learning machine 912 may perform regression analysis on each element of the laser parameter set to determine whether any of the elements are more heavily correlated with an error. The learning machine 912 may suggest an adjustment to the algorithm itself to address an individual element of the laser parameter set.

In an aspect, the algorithm component 910 may limit the adjustment to the algorithm by the neural network predicted error. For example, the neural network 920 may produce an extreme value in the case of an out-of-bounds case where the neural network 920 does not have good training data. The algorithm component 910 may limit the value of the predicted error. For example, the algorithm component 910 may limit the neural network predicted error never to exceed +/−0.5 diopters.

In an aspect, the neural network 920 may be adjusted based on a new ocular measurement. For example, in an implementation, the neural network 920 was provided with both pre-operative and post-refractive measurements of patients who had previously had laser-assisted in-situ keratomileusis (LASIK). The post-refractive measurements can be viewed as an error in the algorithm due to the previous refractive surgery. Being trained based on the difference for the pre-operative measurements and post-refractive measurements, the neural network 920 may provide a correction to the result provided by the algorithm component 910.

Figure 5:
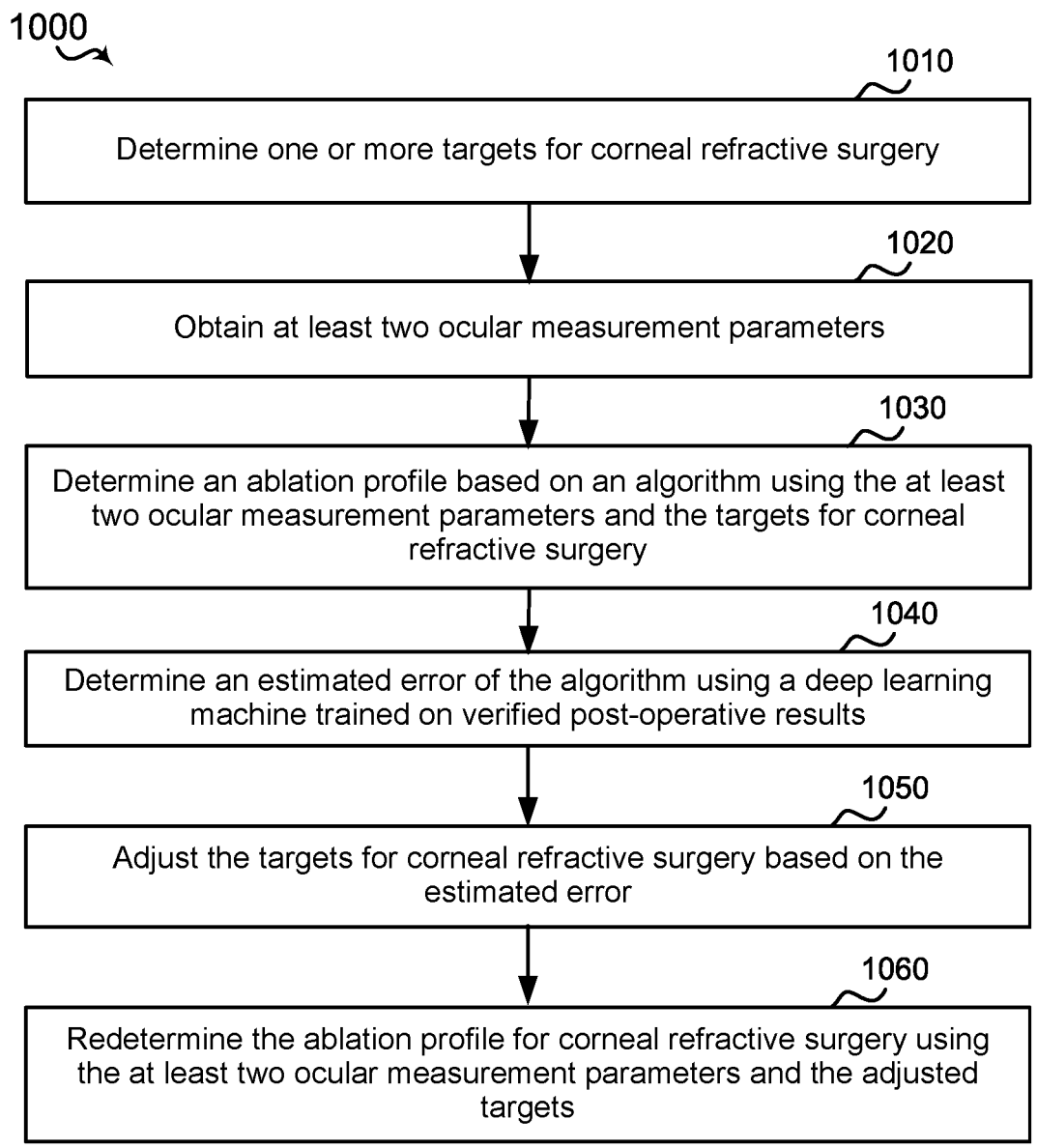
FIG. 5 is a flowchart of an example method for recommending an ablation profile according to an aspect of the disclosure.

FIG. 5 is a flowchart illustrating an example method 1000 of providing a laser parameter set for corneal refractive surgery. The method 1000 may be performed by the system 900.

In block 1010, the method 1000 includes determining one or more targets for corneal refractive surgery. In an aspect, for example, the UI 500 may determine the one or more targets for corneal refractive surgery. In an implementation, the UI 500 may obtain the one or more targets for corneal refractive surgery from an input by an operator. For example, the operator may input a target refraction (e.g., 0 diopters).

In block 1020, the method 1000 includes obtaining at least two ocular measurement parameters. In an aspect, for example, the UI 500 may obtain the at least two measurement parameters, for example, as input from the operator. In another implementation, the measurement parameters may be obtained from an ocular measurement device 466. The ocular measurement parameters may include, for example, axial length, corneal power, corneal power index, and anterior chamber depth. In an aspect, the ocular measurement parameters may include intraoperative aberrometry measurements such as sphere, cylinder, and axis of the eye. In an aspect, the ocular measurement parameters may include one or more of corneal power (keratometry), corneal topography, corneal tomography, corneal pachymetry, refraction, cyclopegia refraction, or wavefront refraction.

In block 1030, the method 1000 may include determining a laser parameter set based on an algorithm using the at least two ocular measurement parameters and the targets for corneal refractive surgery. For example, the algorithm component 910 may determine the laser parameter set based on the algorithm using the at least two ocular measurement parameters.

In block 1040, the method 1000 may include determining an estimated error of the algorithm using a deep learning machine trained on verified post-operative results. In an aspect, for example, the neural network 920 may determine the estimated error of the algorithm. The neural network 920 may have been trained on training sets 930 including verified post-operative results including post-operative refractions corresponding to laser parameter sets. The verified post-operative results may be obtained from a measurement device such as an autorefractor or a wavefront analyzer.

In block 1050, the method 1000 includes adjusting the targets for corneal refractive surgery based on the estimated error. In an aspect, for example, the algorithm component 910 may adjust the targets for corneal refractive surgery based on the estimated error. For instance, the algorithm component 910 may subtract the estimated error from a user input target based on the estimated error.

In block 1060, the method 1000 includes redetermining the laser parameter set for corneal refractive surgery using the at least two ocular measurement parameters and the adjusted targets. In an aspect, for example, the algorithm component 910 may redetermine the laser parameter set for corneal refractive surgery using the at least two ocular measurement parameters and the adjusted targets.

Figure 6:
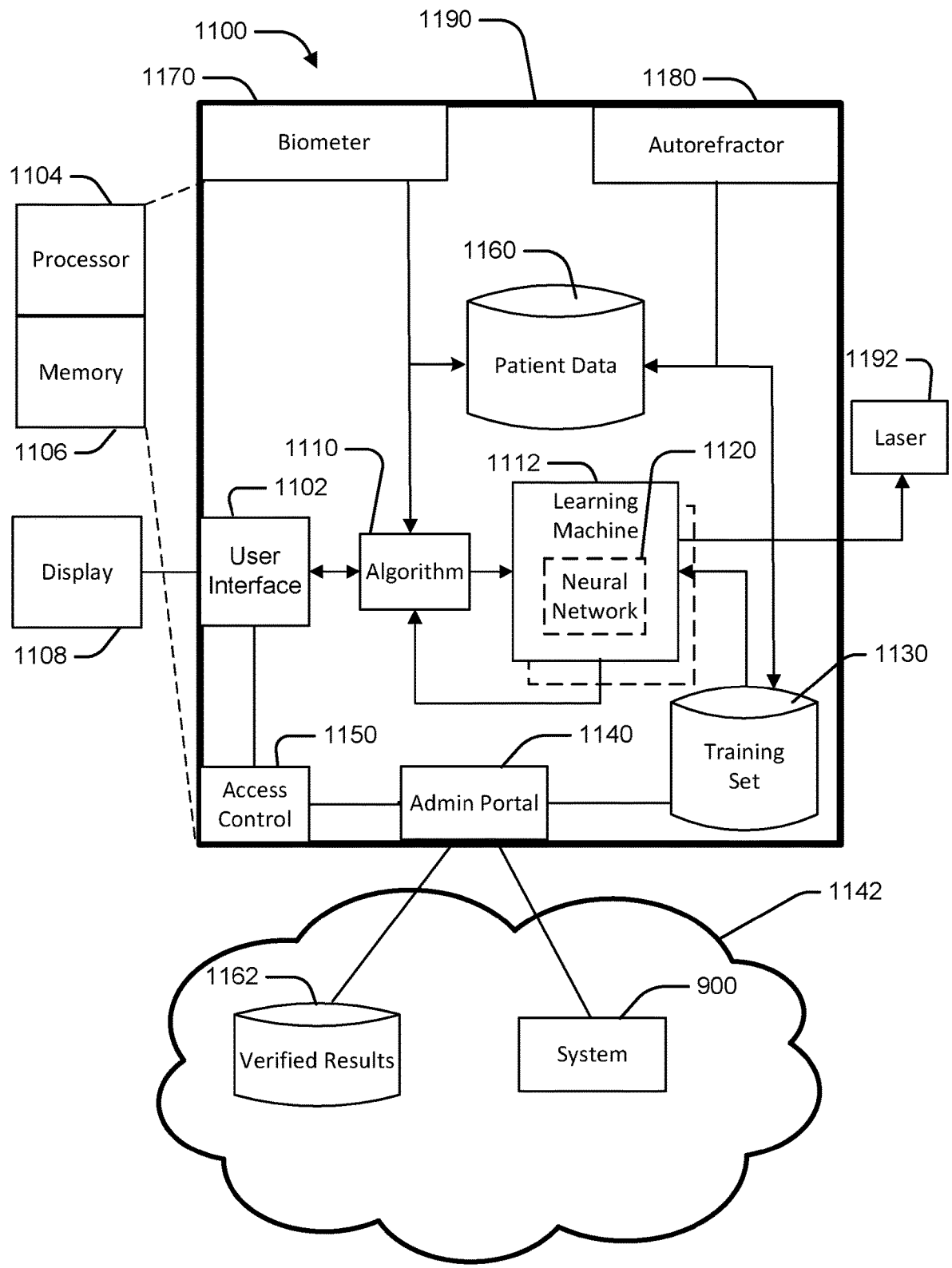
FIG. 6 is a diagram of an example apparatus according to an aspect of the present disclosure.

Turning now to FIG. 6, an example apparatus 1100 may combine various portions of the system 900 with medical diagnostic equipment to provide a single apparatus that implements all or part of the system 900. For example, the apparatus 1100 may recommend a laser parameter set based on an algorithm and a trained deep learning machine 1112. It should be appreciated that while in an example implementation the apparatus 1100 may physically include multiple components within a single case 1190, the apparatus 1100 may also be implemented as interconnected components, which may or may not be physically co-located. For example, in an aspect, verified results from multiple apparatuses 1100 may provide post-operative measurements to a network located database in addition to or instead of using the post-operative measurements locally. Some components of the apparatus 1100 may be implemented as computer-executable instructions stored on a computer-readable medium such as memory 1106. The instructions may be executed by a processor 1104. In an aspect, the processor 1104 and the memory 1106 may reside within the case 1190. Additionally, the apparatus 1100 may include a display 1108, which may display a user interface 1102. The display 1108 may be a touch sensitive screen that receives input from a user. Alternative or additional input/output devices may be included.

In an aspect, the example apparatus 1100 may include a biometer 1170 and an autorefractor 1180 for obtaining measurements of an eye. The biometer 1170 may obtain physical characteristics of the eye such as, but not limited to, corneal power, axial length, anterior chamber depth, corneal power index, a white-to-white distance, and/or lens thickness. The autorefractor 1180 may obtain optical measurements of the eye such as, but not limited to, the refraction of the eye, sphere, cylinder, and axis. In an aspect, the autorefractor 1180 may perform other vision assessment functions including aberrometry, topography, keratometry, and pupillometry. For example, the autorefractor 1180 may include a wavefront analyzer or be referred to as a wavefront analyzer. Conventionally, biometers and autorefractors are separate devices that are used for different purposes. For example, a biometer may be used to obtain measurements for selecting an intraocular lens, whereas an autorefractor may be used to estimate a patient's prescription for eyeglasses or contact lenses. In an aspect, the biometer 1170 and the autorefractor 1180 may be located in separate sensor heads of the apparatus 1100. The apparatus 1100 may include a single chinrest for positioning the patient with respect to one of the sensor heads. Each sensor head may be moved with respect to the chinrest to position the head for obtaining the respective measurements. It should be appreciated that various alternative physical arrangements of the biometer 1170 and autorefractor 1180 may be constructed. In an aspect, for corneal refractive surgery, the biometer 1170 may be optional and all ocular measurement parameters may be obtained from the autorefractor 1180.

In an aspect, the biometer 1170 and the autorefractor 1180 may store measurements in a patient data storage 1160. The patient data storage 1160 may be a computer memory, preferably a non-volatile computer memory such as a hard disc drive, solid state drive, EEPROM, etc. The biometer 1170 and the autorefractor 1180 may access a file of a patient in the patient data storage 1160 and directly record measurements. Such automatic recording may reduce manual transcription errors. In an alternative implementation, the patient data storage 1160 may be stored externally such as, for example, on a doctor's patient management system or a network storage system, in which case the apparatus 1100 may electronically communicate with the external storage.

The apparatus 1100 may include a user interface 1102. The user interface 1102 may guide a user (e.g., a technician) through operating the biometer 1170 and autorefractor 1180 to obtain measurements from a patient. The user interface 1102 may also include user interfaces similar to the user interface 500 (FIG. 3). The user interface 1102 may automatically import measurements into the input field 510 from the patient data storage 1160. The user interface 1102 may receive input from the target refraction field 517.

The algorithm component 1110 may be similar to the algorithm component 910. The algorithm component 1110 may receive the ocular measurements directly from the biometer 1170, the autorefractor 1180, or from the patient data storage 1160. The algorithm component 1110 may implement any of the laser parameter set determination algorithms described herein or known in the art.

The algorithm component 1110 may provide the determined laser parameter set to the learning machine 1112 along with all of the input measurements and parameters. The learning machine 1112 may be similar to the learning machine 912 and include, for example, a neural network 1120. The learning machine 1112 may use deep learning techniques to predict error of the algorithm component 1110 based on the training set 1130 including post-operative results. In an aspect, the training set 1130 may include post-operative results received from the autorefractor 1180. In an aspect, the training set 1130 may include post-operative results from only the autorefractor 1180 such that the trained learning machine 1112 is specific for the apparatus 1100. That is, by training the learning machine 1112 based on input measurements and post-operative results from a single apparatus, the apparatus 1100 may be calibrated to correct for previous errors. In another aspect, the training set 1130 may be combined with other verified results 1162 such as results from other apparatuses 1100, which may be remotely located. The administration portal 1140 may receive and authenticate the verified results 1162, for example, from a trusted web service. In an aspect, the access control 1150 may be accessed by a user via the user interface 1102 to specify which training set 1130 to use.

The apparatus 1100 may include a laser 1192 that is used in performing corneal refractive surgery. For example, the laser 1192 may include an excimer laser, a femtosecond laser, or a combination of one or more of each type of laser. The laser 1192 may receive the final laser parameter set from the learning machine 1112. The laser 1192 may perform ablation according to the final laser parameter set for a LASIK procedure.

In another aspect, some functionality of apparatus 1100 may be performed via network service 1142. For example, the algorithm component 1110 may be periodically updated based on results of machine learning performed remotely. For example, the system 900 may provide the network service 1142. The system 900 may periodically generate an updated algorithm, e.g., based on learning machine 912, and provide the updated algorithm to the algorithm component 1110 via the network service 1142. In that case, the learning machine 1112 and training set 1130 may be remotely located (e.g., as learning machine 912 and training set 930). The admin portal 1140 may be used to receive the updated algorithm component 1110.

In another aspect, the apparatus 1100 may retain a local learning machine 1112, which may be trained by the network service 1142 or system 900. The apparatus 1100 may transmit correlated pre-operative and post-operative measurements to the network service 1142 via the admin portal 1140. The system 900 may then train a learning machine 912 based on a training set 930 including the correlated pre-operative and post-operative measurements of apparatus 1100. The system 900 may then provide the trained learning machine 1112 to the apparatus 1100 for installation. Accordingly, the apparatus 1100 may utilize the trained learning machine 1112 without performing training and without accessing verified results of other apparatuses 1100, which may include confidential data or protected health information (PHI).

Figure 7:
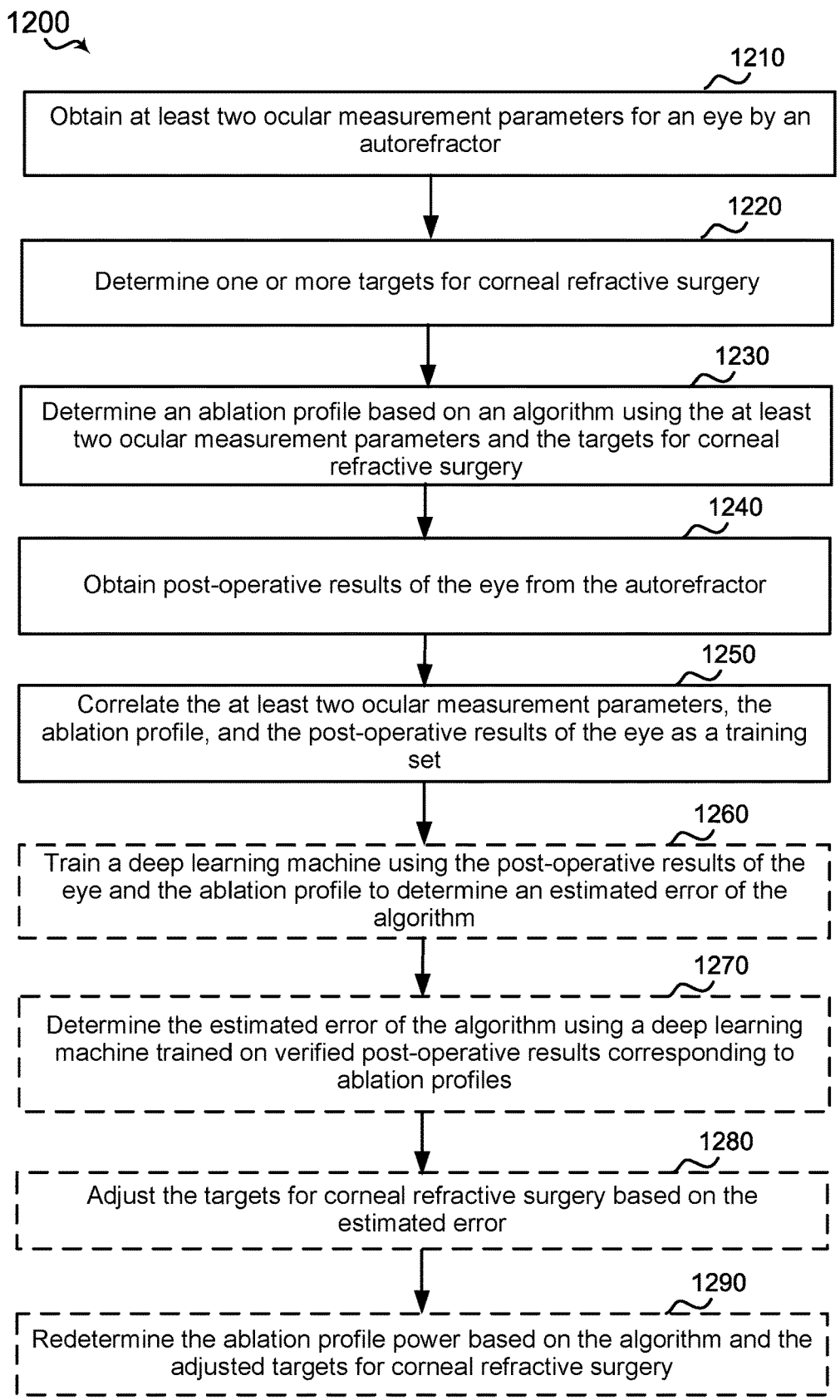
FIG. 7 is a flowchart of a second example method for recommending an ablation profile according to an aspect of the disclosure.

FIG. 7 is a flowchart illustrating an example method 1200 of providing a recommended laser parameter set for corneal refractive surgery. The method 1200 may be performed by the apparatus 1100. The method 1200 may include some similar blocks to the method 1000. It should be appreciated that the methods 1000 and 1200 may be combined. For brevity, description of some duplicate blocks is omitted. Further, as described above, the system 900 may perform some optional blocks of the method 1200.

In block 1210, the method 1200 includes obtaining at least two ocular measurement parameters for an eye by an autorefractor. In an aspect, for example, the autorefractor 1180 may obtain the at least two ocular measurement parameters and a lens selection parameter for an eye. In an implementation, the autorefractor 1190 may obtain the parameters for both eyes of a patient. The ocular measurement parameters may include, for example, corneal power (keratometry), corneal topography, corneal tomography, corneal pachymetry, refraction, cyclopegia refraction, or wavefront refraction.

In block 1220, the method 1200 includes determining one or more targets for corneal refractive surgery. In an implementation, the user interface 1102 may determine the one or more targets for corneal refractive surgery. For example, the targets for corneal refractive surgery may be a target refraction for the eye following the corneal refractive surgery. The one or more targets for corneal refractive surgery may be entered by a technician or an ophthalmologist.

In block 1230, the method 1200 includes determining a laser parameter set based on an algorithm using the at least two ocular measurement parameters and the targets for corneal refractive surgery. For example, the algorithm component 1110 may determine the laser parameter set based on an algorithm using the at least two ocular measurement parameters and the targets for corneal refractive surgery.

In block 1240, the method 1200 may include obtaining a post-operative refraction of the eye from the autorefractor. In an aspect, for example, the autorefractor 1180 may obtain the post-operative refraction of the eye. In an aspect, the autorefractor 1180 may be coupled to the biometer 1170 (if used to obtain ocular measurement parameters) such that the same apparatus is used to obtain the at least two ocular measurement parameters and the post-operative refraction. Additionally, the measurements may be stored in a common patient data storage 1160.

In block 1250, the method 1200 may include correlating the at least two ocular measurement parameters, the laser parameter set, and the post-operative refraction as a training set. Since the biometer 1170 and the autorefractor 1180 are communicatively coupled, or the autorefractor 1180 is used to obtain both pre and post-operative measurements, the training set can be correlated directly from the devices without need for human data entry, which may result in transcription errors. Further, consistency may be improved by generating multiple data sets using a known pair of biometer 1170 and autorefractor 1180, or the same device for pre and post-operative measurements.

In block 1260, the method 1200 optionally includes training a deep learning machine using the post-operative refraction of the eye and the laser parameter set to determine an estimated error of the algorithm. In an aspect, the apparatus 1100 may train the learning machine 1112 using the post-operative refraction of the eye and the laser parameter set. The learning machine 1112 may be trained to estimate the error of the algorithm component 1110 for a particular set of input parameters including the at least two ocular measurement parameters and the laser parameter set. The learning machine 1112 may be trained by providing the training sets labeled with the post-operative refraction as the result. It should be understood that the learning machine 1112 may be trained on training data from previous procedures. The at least two ocular measurement parameters for a current procedure may not be included in the training data because the post-operative refraction is not available. Once the post-operative refraction becomes available, the complete training set may be used to further train or retrain the learning machine 1112. In an aspect, the block 1260 may be performed by an external system such as the system 900, which may communicate with the apparatus 1100 via a network service 1142. The apparatus 1100 may receive the trained learning machine 1112 via the network service 1142.

In block 1270, the method 1200 may optionally include determining an estimated error of the algorithm using a deep learning machine trained on verified post-operative results including post-operative refractions corresponding to the laser parameter set. In an aspect, for example, the learning machine 1112 may determine the estimated error of the algorithm. As discussed above, the learning machine 1112 may have been trained on training sets 1130 or 930 including verified post-operative results including post-operative refractions corresponding to the laser parameter set.

In block 1280, the method 1200 may optionally include adjusting the targets for corneal refractive surgery based on the estimated error. In an aspect, for example, the algorithm component 1110 may adjust the targets for corneal refractive surgery based on the estimated error. For instance, the algorithm component 1110 may subtract the estimated error from a user input lens selection parameter.

In block 1290, the method 1200 may optionally include redetermining the laser parameter set based on the algorithm and the adjusted targets for corneal refractive surgery. In an aspect, for example, the algorithm component 1110 may redetermine the laser parameter set based on the algorithm and the adjusted targets for corneal refractive surgery.

Figure 8:
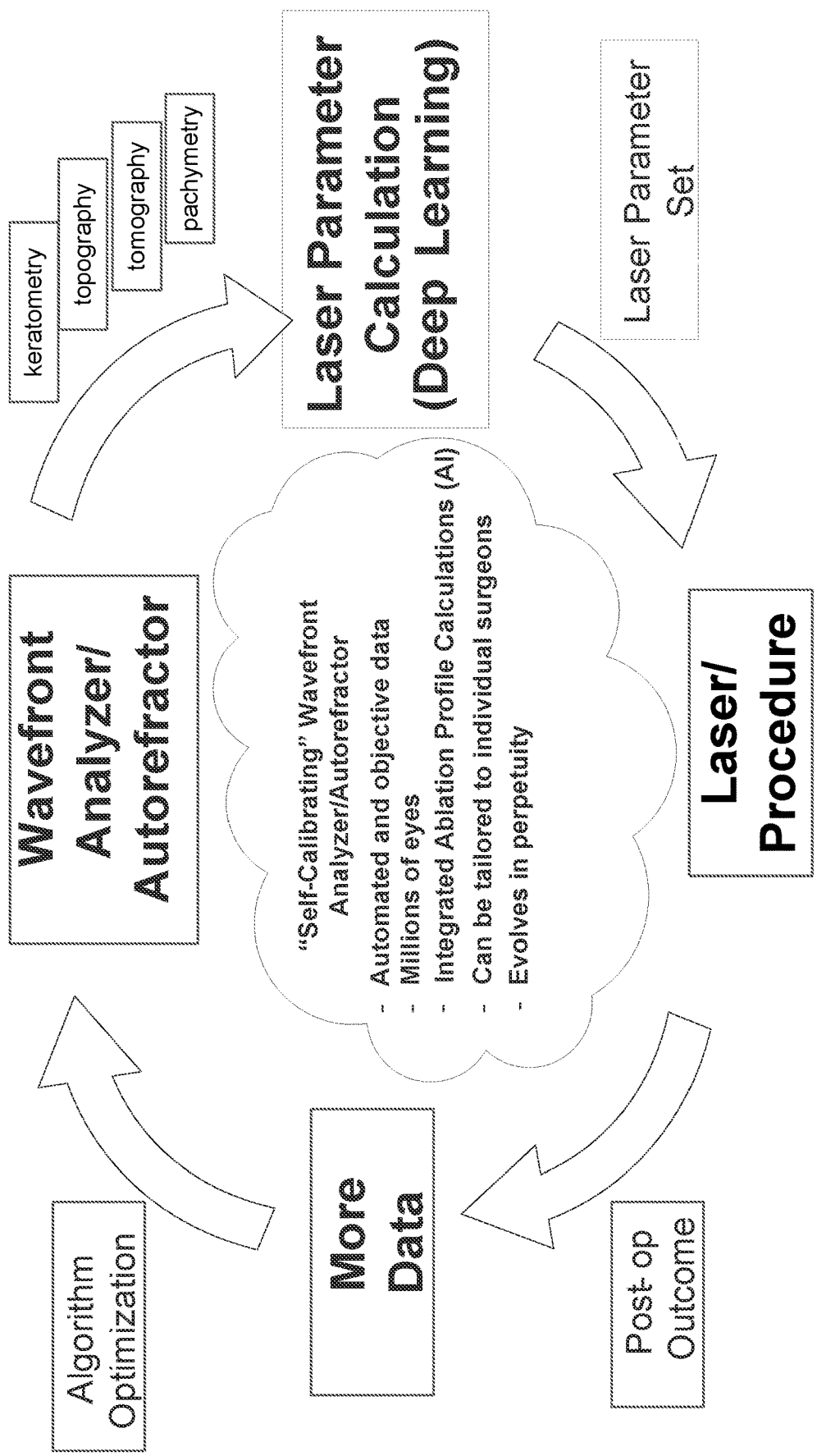
FIG. 8 is a conceptual diagram illustrating an example use context for the example apparatus of FIG. 6.

FIG. 8 is a conceptual diagram illustrating an example use context for the example apparatus 1100. The apparatus 1100 may be referred to as a self-calibrating autorefractor or laser. The apparatus 1100 may automate collection of objective data that can be used to calibrate the apparatus 1100. For example, laser parameter set determinations of the apparatus 1100 may be improved using deep learning to analyze post-operative results obtained via the autorefractor 1180. The apparatus 1100 may continually improve as additional data is collected.

While aspects of the present disclosure have been described in connection with examples thereof, it will be understood by those skilled in the art that variations and modifications of the aspects of the present disclosure described above may be made without departing from the scope hereof. Other aspects will be apparent to those skilled in the art from a consideration of the specification or from a practice in accordance with aspects of the disclosure disclosed herein.

The invention claimed is:

1. A method for determining a laser parameter set for corneal refractive surgery, comprising:
   determining one or more targets for corneal refractive surgery;
   obtaining at least two ocular measurement parameters of an eye;
   determining a laser parameter set based on an algorithm using the at least two ocular measurement parameters and the one or more targets for corneal refractive surgery;
   determining an estimated error of the algorithm using a deep learning machine trained on verified post-operative results;
   adjusting the one or more targets for corneal refractive surgery based on the estimated error;
   redetermining the laser parameter set for corneal refractive surgery; and
   configuring a laser to emit a laser beam based on the redetermined laser parameter set.

2. The method of claim 1, wherein the laser parameter set includes one or more of ablation diameter, ablation depth, ablation blend zone, corneal flap thickness, residual corneal bed, excimer fluence level, femtosecond laser flap size, or type of femtosecond laser used.

3. The method of claim 1, wherein the at least two ocular measurement parameters include at least two of: corneal power (keratometry), corneal topography, corneal tomography, corneal pachymetry, refraction, cyclopegia refraction, or wavefront refraction.

4. The method of claim 1, wherein the verified post-operative results include one or more of: post-operative inflammation, post-op corneal power (keratometry), post-op corneal topography, post-op corneal tomography, post-op corneal pachymetry, or post-op refraction.

5. The method of claim 1, further comprising training the deep learning machine using a training set including at least the two ocular measurement parameters of the eye and the verified post-operative results for the eye to determine the estimated error of the algorithm.

6. The method of claim 5, wherein the training set includes the one or more targets for corneal refractive surgery.

7. The method of claim 1, wherein the one or more targets for corneal refractive surgery includes a target refraction.

8. The method of claim 1, wherein the algorithm for determining the laser parameter set includes a wavefront guided profile, a wavefront-optimized profile, or a topography-guided profile, or adjustments thereto.

9. The method of claim 1, wherein the laser parameter set is for a laser-assisted in-situ keratomileusis (LASIK) procedure or Small Incision Lenticule Extraction (SMILE) procedure.

10. A method of laser parameter set selection, comprising:
obtaining at least two ocular measurement parameters for an eye by an autorefractor;
determining one or more targets for corneal refractive surgery;
determining a laser parameter set based on an algorithm using the at least two ocular measurement parameters;
configuring a laser to emit a laser beam based on the laser parameter set;
obtaining a post-operative refraction of the eye from the autorefractor;
correlating the at least two ocular measurement parameters, the laser parameter set, and the post-operative refraction as a training set; and
training a deep learning machine using the post-operative refraction of the eye and the laser parameter set to determine an estimated error of the algorithm.

11. The method of claim 10, further comprising:
determining an estimated error of the algorithm using a deep learning machine trained on verified post-operative results including post-operative refractions corresponding to laser parameter sets;
adjusting the one or more targets for corneal refractive surgery based on the estimated error; and
redetermining a final laser parameter set based on the algorithm and the adjusted one or more targets for corneal refractive surgery.

12. The method of claim 11, wherein correlating the at least two ocular measurement parameters, the laser parameter set, and the post-operative refraction as the training set comprises including the final laser parameter set in the training set.

13. The method of claim 10, wherein the one or more targets for corneal refractive surgery is a target refraction.

14. The method of claim 10, wherein the at least two ocular measurement parameters are selected from the group consisting of: corneal power (keratometry), corneal topography, corneal tomography, corneal pachymetry, refraction, cyclopegia refraction, and wavefront refraction.

15. The method of claim 10, wherein the algorithm for determining the laser parameter set includes one or more of: a wavefront guided profile, a wavefront-optimized profile, or a topography-guided profile, or adjustments thereto.

16. A non-transitory computer-readable medium storing computer executable instructions, comprising instructions to cause a computer to:
obtain at least two ocular measurement parameters for an eye by an autorefractor or a wavefront analyzer;
determine one or more targets for corneal refractive surgery;
determine a laser parameter set based on an algorithm using the at least two ocular measurement parameters;
determine an estimated error of the algorithm using a deep learning machine trained on verified post-operative results;
adjust the one or more targets for corneal refractive surgery based on the estimated error;
redetermine the laser parameter set for corneal refractive surgery;
configure a laser to emit a laser beam based on the redetermined laser parameter set;
obtain a post-operative refraction of the eye from the autorefractor or the wavefront analyzer; and
correlate the at least two ocular measurement parameters, the laser parameter set, and the post-operative refraction as a training set.

17. An apparatus for determining a laser parameter set for corneal refractive surgery, comprising:
an autorefractor configured to obtain at least two ocular measurement parameters for an eye and to obtain a post-operative refraction of the eye;
a user interface configured to obtain a target refraction for the eye;
a memory; and
a processor communicatively coupled to the user interface, the autorefractor, and the memory, and configured to:
determine the laser parameter set based on an algorithm using the at least two ocular measurement parameters;
correlate the at least two ocular measurement parameters, the laser parameter set, and the post-operative refraction as a training set; and
train a deep learning machine using the post-operative refraction of the eye and the laser parameter set to determine an estimated error of the algorithm.

18. The apparatus of claim 17, wherein the processor is configured to:
determine an estimated error of the algorithm using a deep learning machine trained on verified post-operative results including post-operative refractions corresponding to laser parameter sets;
adjust the target refraction for the eye based on the estimated error; and
redetermine a final laser parameter set based on the algorithm and the adjusted target refraction for the eye.

19. The apparatus of claim 18, further comprising a laser for performing the corneal refractive surgery based on the final laser parameter set.

* * * * *